United States Patent [19]
Yamazaki et al.

[11] Patent Number: 5,932,178
[45] Date of Patent: Aug. 3, 1999

[54] FDG SYNTHESIZER USING COLUMNS

[75] Inventors: Shigeki Yamazaki, Moriya-Machi; Katsuhiko Ohsaki, Kawasaki, both of Japan

[73] Assignees: NKK Plant Engineering Corporation, Yokohama; NKK Corporation, Tokyo, both of Japan

[21] Appl. No.: 08/824,566

[22] Filed: Mar. 26, 1997

[30] Foreign Application Priority Data

| Mar. 29, 1996 | [JP] | Japan | 8-075532 |
| Mar. 29, 1996 | [JP] | Japan | 8-075533 |
| Mar. 29, 1996 | [JP] | Japan | 8-075534 |
| Mar. 29, 1996 | [JP] | Japan | 8-075535 |
| Mar. 29, 1996 | [JP] | Japan | 8-075536 |

[51] Int. Cl.$^6$ .................. G21C 1/00; G21G 1/06
[52] U.S. Cl. .................. 422/159; 422/DIG. 903; 376/168
[58] Field of Search .................. 536/18.5; 422/159, 422/216, DIG. 903; 376/168

[56] References Cited

U.S. PATENT DOCUMENTS

| H74 | 6/1986 | Shiue et al. | 536/124 |
| 4,617,386 | 10/1986 | Elmaleh et al. | 536/122 |
| 5,759,513 | 6/1998 | Nakazawa | 424/1.11 |
| 5,808,020 | 9/1998 | Ferrieri et al. | 536/18.5 |

FOREIGN PATENT DOCUMENTS

| 0 588 480 | 3/1994 | European Pat. Off. . |
| 6-157572 | 6/1994 | Japan . |
| WO 94/21653 | 9/1994 | WIPO . |
| WO97/42203 | 11/1997 | WIPO . |

OTHER PUBLICATIONS

G. Keith Mulholland, "Simple Rapid Hydrolysis of Acetyl Protecting Groups in the FDG Synthesis Using Cation Exchange Resins", Nucl. Med. Biol., 22, 19–23, (1995).

Toorongian et al, "Routine Production of 2–deoxy–2–[$^{18}$F] fluoro–D–glucose by Direct Nucleophilic Exchange on a Quaternary 4–aminopyridinium Resin", Nucl. Med. Biol. vol. 17, No. 3, 1990, pp. 273–279.

Hamacher et al, "Efficient Stereospecific Synthesis of No–Carrier–Added 2–[$^{18}$F]–fluoro–2–deoxy–D–glucose Using Aminopolyether Supported Nucleophilic Substitution", The Journal of Nuclear Medicine, vol. 27, No. 2, Feb. 1986, pp. 235–238.

M. Diksic and D. Jolly, "New High–Yield Synthesis of $^{18}$F–Labelled 2–deoxy–2–fluoro–D–glucose", Int. J. Appl. Radiat. Isot, vol. 34, No. 6, 1983, pp. 893–896.

Haradahira et al, A New Synthesis of 2–deoxy–2–[$^{18}$F] fluoro–D–galactose Using [$^{18}$F] fluoride ion, Journal of Labelled Compounds and Radiopharmaceuticals, vol. XXV, No. 7, 1988, pp. 721–729.

*Primary Examiner*—Nina Bhat
*Attorney, Agent, or Firm*—Frishauf, Holtz, Goodman, Langer & Chick, P.C.

[57] ABSTRACT

An FDG synthesizer, which comprises: a labeling reaction resin column comprising a column filled with a polymer-supported phase-transfer catalyst resin for trapping an [$^{18}$F] fluoride ion contained in a target water, and performing a labeling reaction between the thus trapped [$^{18}$F] fluoride ion and triflate, on the one hand, and a hydrolysis reaction vessel for receiving a reaction intermediate product obtained from the labeling reaction, and performing a hydrolysis reaction by adding a strong acidic aqueous solution or a strong alkaline aqueous solution thereto, on the other hand. The above-mentioned hydrolysis reaction vessel may be replaced with a cation-exchange resin column having a heating device and a flow rate control device of the reaction intermediate product.

10 Claims, 6 Drawing Sheets

1

FDG SYNTHESIZER USING COLUMNS

REFERENCE TO PATENTS, APPLICATIONS AND PUBLICATIONS PERTINENT TO THE INVENTION

As far as we know, there is available the following prior art document pertinent to the present invention:

Japanese Patent Provisional Publication No. 6-157,572 laid open as of Jun. 3, 1994

The contents of the prior art disclosed in the above-mentioned prior art document will be discussed later under the heading of "BACKGROUND OF THE INVENTION".

BACKGROUND OF THE INVENTION

Field of the Invention

The present invention relates to a synthesizer of fluoro-deoxy glucose (hereinafter referred to as "FDG") used as a labeled compound in a positron emission tomography (hereinafter referred to as "PET") system.

RELATED ART STATEMENT

As a method for observing and diagnosing the state in a human body by means of an image in the medical field, the image diagnosis based on a PET system using a substance emitting positron is now attracting the general attention. According to the image diagnosis based on the PET system, it is possible to obtain not only a formal image of diseases such as a cancer but also a functional image of the motion of blood or oxygen in a human body, thus displaying a remarkable power in the diagnosis of a brain damage or a cardial malady.

The PET system is an image diagnosis system using a radioactive isotope having a short half-value period, and substantially comprises the following steps of:

(1) accelerating ions to a high energy in a cyclotron;
(2) producing a radionuclide by irradiating the thus accelerated ions to a material referred to as a target in a target box which is a reactor;
(3) using the thus produced radionuclide as a raw material, and preparing a compound labeled with a radioactive isotope capable of being administered to a human body in a labeled compound synthesizer; and
(4) administering the thus prepared labeled compound to a human body, detecting a distribution of the labeled compound incorporated in the human body by means of a scanner, and converting the result of detection into an image by a computer.

As a labeled compound for the PET system, there is known fluoro-deoxy-glucose, i.e., FDG. FDG is a labeled compound in which a part of glucose is substituted with an [$^{18}$F] fluoride ion which is a positron emission nuclide (the half-value period thereof being 119.7 minutes), and is used for the diagnosis of a brain function and a malignant tumor.

As a method for synthesizing FDG, there is known the method proposed by Hamacher et al. This method of synthesis comprises a step of a labeling reaction for combining an [$^{18}$F] fluoride ion which is a radioactive isotope (also referred to as a radionuclide or a positron emission nuclide) with a compound, and a step of a hydrolysis reaction for separating a protecting group (usually, an acetyl group) from a reaction intermediate product obtained from the labeling reaction.

A method for synthesizing FDG (hereinafter referred to as the "prior art") is disclosed in Japanese Patent Provisional Publication No. 6-157,572 laid open as of Jun. 3, 1994, which will be described with reference to FIG. 1:

Proton particles accelerated in a cyclotron (not shown) are irradiated onto O-18($^{18}$O) water in a target box 1 to produce an [$^{18}$F] fluoride ion. The O-18($^{18}$O) water containing the thus produced [$^{18}$F] fluoride ion (hereinafter referred to as the "target water") is taken out from the target box 1, and, as shown in FIG. 1, sent to a target water container 2. Then, the target water is passed through an anion-exchange resin 3 from the target water container 2 to trap the [$^{18}$F] fluoride ion in the target water by means of the anion-exchange resin, and the remaining target water is recovered in a target water recovery container 4.

Then, a potassium carbonate aqueous solution is sucked up from a potassium carbide aqueous solution container 5 by means of a syringe 6, and is passed through the anion-exchange resin 3 to extract the [$^{18}$F] fluoride ion trapped by means of the anion-exchange resin 3. The thus extracted [$^{18}$F] fluoride ion is sent to a reaction vessel 7. Then, an acetonitrile solution of kryptofix 222 is sent from a kryptofix 222 container 8 to the reaction vessel 7. Subsequently, the reaction vessel 7 thus receiving the [$^{18}$F] fluoride ion and the acetonitrile solution of kryptofix 222 is heated to evaporation-eliminate moisture in the reaction vessel 7. Then, after the elimination of moisture in the reaction vessel 7, acetonitrile is sucked up from an acetonitrile container 9 by means of a syringe 10, and is sent to the reaction vessel 7. Then, the reaction vessel 7 is heated again to ensure a sufficient evaporation-elimination of moisture in the reaction vessel 7.

Then, after the sufficient evaporation-elimination of moisture in the reaction vessel 7, an acetonitrile solution of 1,3,4,6-tetra-O-acetyl-2-O-trifluoromethane-sulfonyl-β-D-mannopyranose (hereinafter referred to as "triflate"), which is a reaction substrate, is sent from a triflate container 11 to the reaction vessel 7. In the reaction vessel 7, a labeling reaction of triflate is performed at a temperature of about 80° C. for about five minutes.

Then, after the completion of the labeling reaction, water is sucked up from a water container 12 by means of a syringe 13, and is sent to the reaction vessel 7. Then, the solution present in the reaction vessel 7 is passed through a SepPak C-18 cartridge 14 from the reaction vessel 7 to cause the cartridge 14 to trap 4-acetyl-FDG which is a reaction intermediate product in the solution. A waste liquid containing non-reacting [$^{18}$F] fluoride ion and kryptofix 222 is sent to a waste liquid recovery container 15. Thus, 4-acetyl-FDG is separated from non-reacting [$^{18}$F] fluoride ion and kryptofix 222.

Then, acetonitrile is sucked up from the acetonitrile container 9 by means of the syringe, and the separated reaction intermediate product, i.e., 4-acetyl-FDG, extracted from the SepPak C-18 cartridge 14, is sent again to the reaction vessel 7. Subsequently, the reaction vessel 7 receiving the above-mentioned acetonitrile and reaction intermediate product is heated to evaporation-eliminate acetonitrile as an organic solvent. Then, a hydrochloric acid aqueous solution is sucked up from a hydrochloric acid aqueous solution container 16 by means of a syringe 17, and added into the reaction vessel 7. Then, the reaction vessel 7 thus added with the hydrochloric acid aqueous solution is heated at a temperature of about 130° C. for 10 to 20 minutes to perform a hydrolysis reaction.

Then, after the completion of the hydrolysis reaction, water is sucked up from the water container 12, and is added into the reaction vessel 7. The thus processed solution in the reaction vessel 7 is then passed sequentially through an ion retardation resin column 18 and a refining column 19, and the synthesized FDG is received in an FDG container 20.

There is also known a method of obtaining a synthesized FDG through the same process as in the prior art except that tetrabutyl ammonium hydrocarbonate (abbreviated as "TBAHCO$_3$") is used in place of kryptofix 222 in the prior art.

In the prior art, a phase transfer catalyst comprising kryptofix 222 or tetrabutyl ammonium hydrocarbonate is added into the reaction vessel during the labeling reaction. The added catalyst therefore remains in the reaction vessel after the completion of the labeling reaction, thus requiring a process for eliminating this phase transfer catalyst. In addition, because of the use of the foregoing phase transfer catalyst, it is necessary to completely eliminate water hindering the labeling reaction through evaporation, and this takes much time. Furthermore, a process using an anion-exchange resin is necessary for recovery of the target water, this poses a problem of a complicated FDG synthesizing process. Since the [$^{18}$F] fluoride ion has a half-value period of about two hours, more processes or more complicated processes lead to a longer period of time for the synthesis, thus resulting in a reduced yield of FDG.

Under such circumstances, there is an increasing demand for development of an FDG synthesizer, in which a synthesizing process is simplified, with an improved yield of a synthesized product, and the time of synthesis is reduced, but such an FDG synthesizer has not as yet been proposed.

SUMMARY OF THE INVENTION

An object of the present invention is therefore to provide an FDG synthesizer, in which a synthesizing process is simplified, with an improved yield of a synthesized product, and the time of synthesis is reduced.

In accordance with one of the features of the present invention, there is provided an FDG synthesizer, which comprises: a labeling reaction resin column comprising a column filled with a polymer-supported phase-transfer catalyst resin for trapping an [$^{18}$F] fluoride ion contained in target water, and performing a labeling reaction between the thus trapped [$^{18}$F] fluoride ion and triflate, on the one hand, and a hydrolysis reaction vessel for receiving a reaction intermediate product obtained from said labeling reaction, and performing a hydrolysis reaction by adding a strong acidic aqueous solution or a strong alkaline aqueous solution, on the other hand.

In accordance with another one of the features of the present invention, there is provided an FDG synthesizer, wherein: said polymer-supported phase-transfer catalyst resin comprises a phosphonium salt fixed to a polystyrene resin or a pyridinium salt fixed to a polystyrene resin.

In accordance with another one of the features of the present invention, there is provided an FDG synthesizer, wherein: said hydrolysis reaction vessel comprises a cation-exchange resin column, and said reaction intermediate product obtained from said labeling reaction is brought into contact with a cation-exchange resin adjusted to an H$^+$ type in said cation-exchange resin column to perform said hydrolysis reaction.

In accordance with another one of the features of the present invention, there is provided an FDG synthesizer, wherein: said hydrolysis reaction vessel comprises a cation-exchange resin column having a heating means and a flow rate control means of said reaction intermediate product containing an organic solvent, and in said cation-exchange resin column, said reaction intermediate product containing said organic solvent obtained from said labeling reaction is heated, to evaporation-eliminate said organic solvent, and at the same time, said reaction intermediate product after the elimination of said organic solvent is brought into contact with a cation-exchange resin adjusted to an H$^+$ type to perform said hydrolysis reaction, thereby simultaneously performing said elimination of organic solvent and said hydrolysis reaction in said cation-exchange resin column.

In accordance with another one of the features of the present invention, there is provided an FDG synthesizer, which comprises: (a) a cartridge-type labeling reaction resin column, (b) a cartridge-type cation-exchange resin column, and (c) a disposable cartridge base into which paths and switchover valves for communicating said labeling reaction resin column and said cation-exchange resin column are incorporated; said cartridge-type labeling reaction resin column comprising a disposable column filled with a polymer-supported phase-transfer catalyst resin, said cartridge-type labeling reaction resin column being one-touch-releasably attachable to said cartridge base, trapping an [$^{18}$F] fluoride ion contained in a target water, and performing a labeling reaction between the thus trapped [$^{18}$F] fluoride ion and triflate; and said cartridge-type cation-exchange resin column comprising a disposable column filled with a cation-exchange resin adjusted to an H$^+$ type, said cartridge-type cation-exchange resin column being one-touch-releasably attachable to said cartridge base, and bringing a reaction intermediate product obtained from said the labeling reaction into contact with said cation-exchange resin adjusted to the H$^+$ type in said cation-exchange resin column to perform a hydrolysis reaction.

DETAILED DESCRIPTION OF PREFERRED EMBODIMENTS

Figure 1:
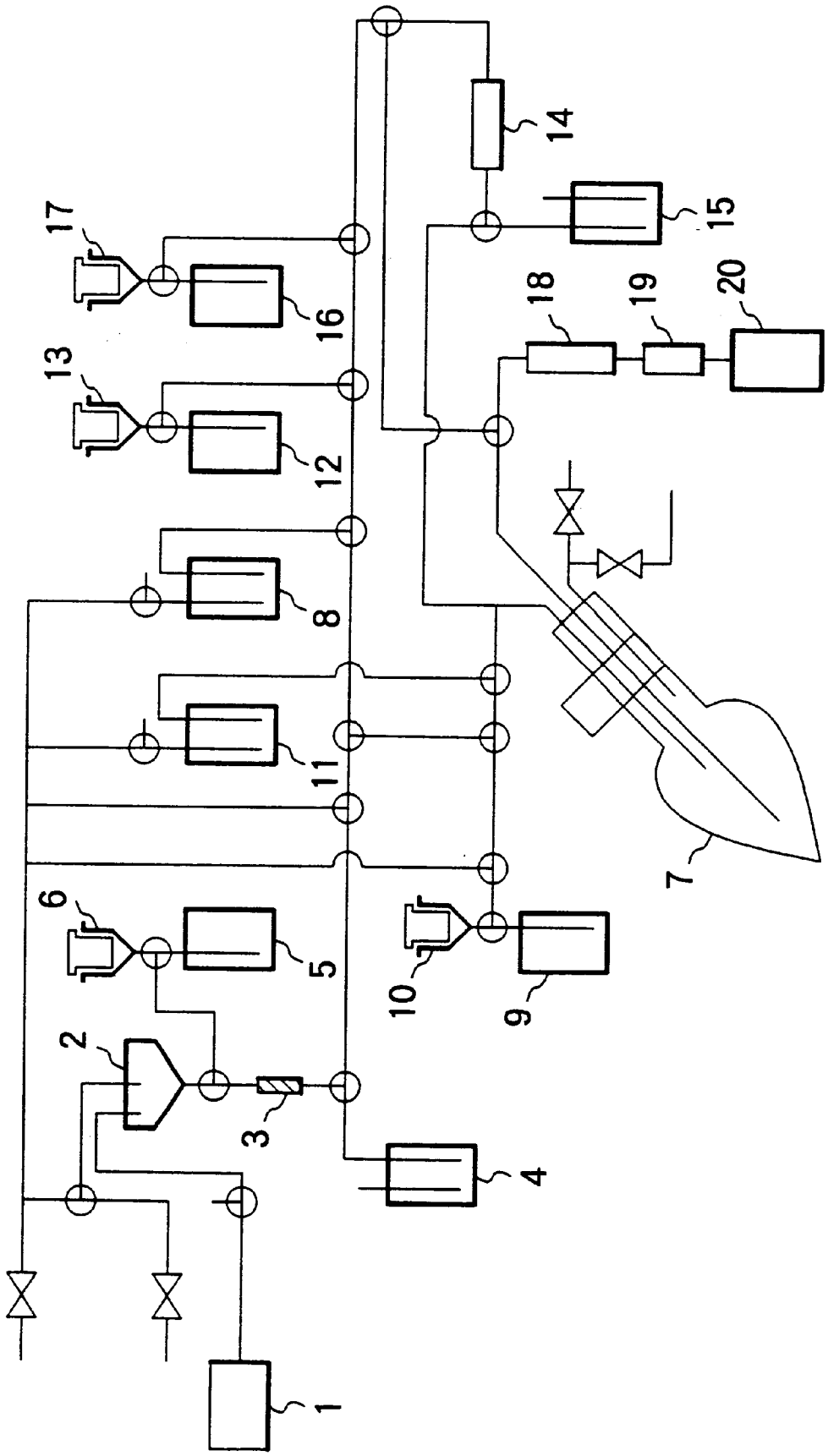
FIG. 1 is a schematic descriptive view illustrating an FDG synthesizing method of the prior art.

From the above-mentioned point of view, extensive studies were carried out to develop an FDG synthesizer, in which a synthesizing process is simplified, with a higher yield of a synthesized product, and the time of synthesis is reduced.

As a result, the following findings were obtained: there is available an FDG synthesizer, in which a synthesizing process is simplified, with an improved yield of a synthesized product and the time of synthesis is reduced, by using a column filled with a polymer-supported phase-transfer catalyst resin obtained by fixing a phosphonium salt or a pyridinium salt to a polystyrene resin in place of a conventional labeling reaction vessel for performing a labeling reaction, and using a column filled with a cation-exchange resin in place of a conventional hydrolysis reaction vessel.

The present invention was developed on the basis of the foregoing findings.

An FDG synthesizer of a first embodiment of the present invention comprises: a labeling reaction resin column comprising a column filled with a polymer-supporter phase-transfer catalyst resin for trapping an [$^{18}$F] fluoride ion contained in a target water, and performing a labeling reaction between the thus trapped [$^{18}$F] fluoride ion and triflate, on the one hand, and a hydrolysis reaction vessel for receiving a reaction intermediate product obtained from said labeling reaction, and performing a hydrolysis reaction by adding a strong acidic aqueous solution or a strong alkaline aqueous solution, on the other hand. The above-mentioned polymer-supporter phase-transfer catalyst resin can be obtained by fixing a phosphonium salt or a pyridinium salt to a polystyrene resin.

An FDG synthesizer of a second embodiment of the present invention is characterized in that said hydrolysis reaction vessel comprises a cation-exchange resin column, and said reaction intermediate product obtained from said labeling reaction is brought into contact with a cation-exchange resin adjusted to an H$^+$ -type in said cation-exchange resin column, to perform the hydrolysis reaction.

An FDG synthesizer of a third embodiment of the present invention is characterized in that said hydrolysis reaction vessel comprises a cation-exchange resin column having a heating means and a flow rate control means of said reaction intermediate product containing an organic solvent, and in said cation-exchange resin column, said reaction intermediate product containing said organic solvent obtained from said labeling reaction is heated, to evaporation-eliminate said organic solvent, and at the same time, the reaction intermediate product after the elimination of said organic solvent is brought into contact with a cation-exchange resin adjusted to an H$^+$ type to perform said hydrolysis reaction, thereby simultaneously performing said elimination of organic solvent and said hydrolysis reaction in said cation-exchange resin column.

An FDG synthesizer of a fourth embodiment of the present invention comprises: (a) a cartridge-type labeling reaction resin column, (b) a cartridge-type cation-exchange resin column, and (c) a disposable cartridge base into which paths and switchover valves for communicating said labeling reaction resin column and said cation-exchange resin column are incorporated; said cartridge-type labeling reaction resin column comprising a disposable column filled with a polymer-supported phase-transfer catalyst resin, said cartridge-type labeling reaction resin column being one-touch-releasably attachable to said cartridge base, trapping an [$^{18}$F] fluoride ion contained in target water, and performing a labeling reaction between the thus trapped [$^{18}$F] fluoride ion and triflate; and said cartridge-type cation-exchange resin column comprising a disposable column filled with a cation-exchange resin adjusted to an H$^+$ type, said cartridge-type cation-exchange resin column being one-touch-releasably attachable to said cartridge base, and bringing a reaction intermediate product obtained from said labeling reaction into contact with said cation-exchange resin adjusted to an H$^+$ type in said cation-exchange resin column to perform a hydrolysis reaction.

Now, the present invention is described below with reference to the drawings.

Figure 2:
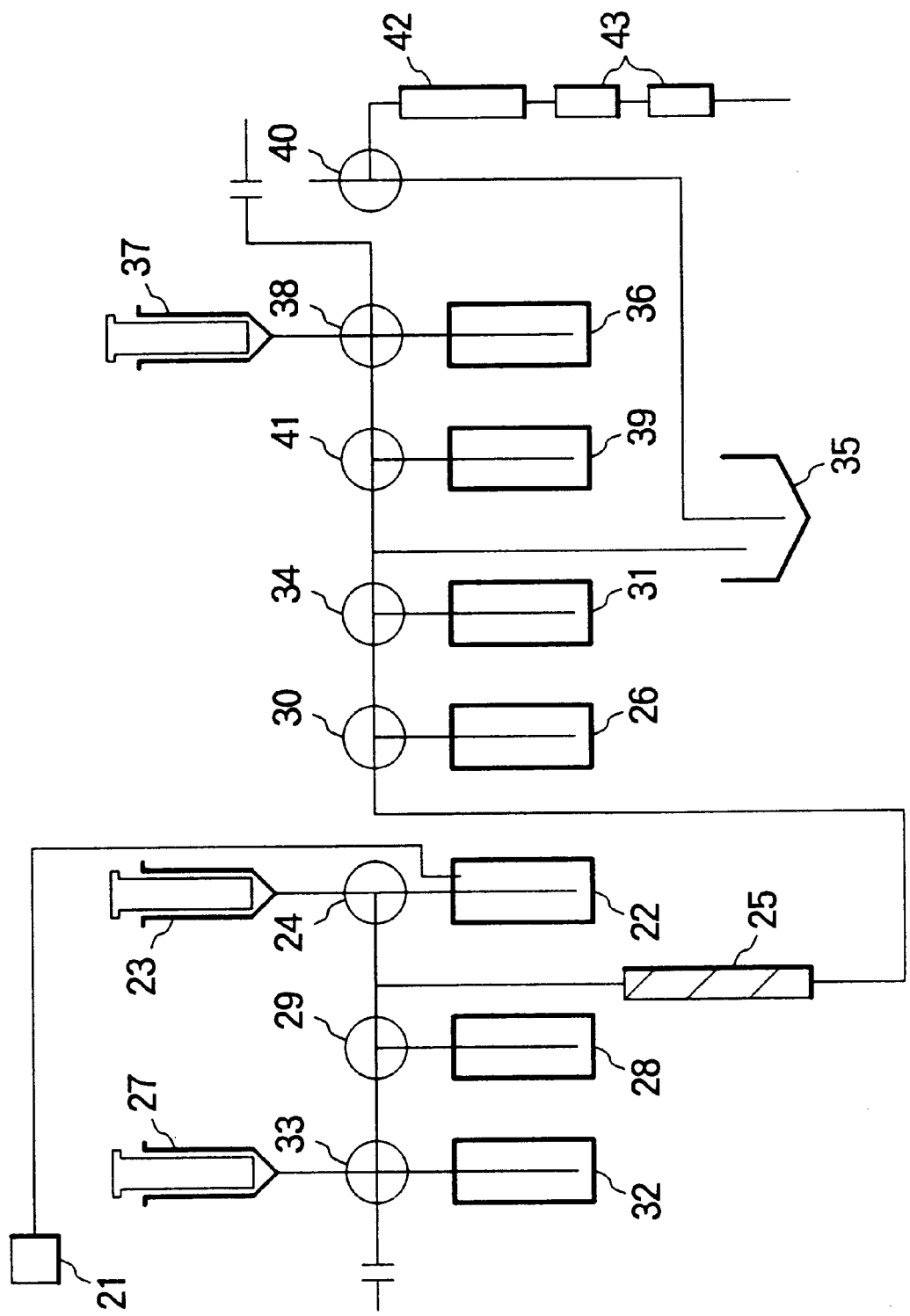
FIG. 2 is a schematic descriptive view illustrating an FDG synthesizer of a first embodiment of the present invention.

FIG. 2 is a schematic descriptive view illustrating the FDG synthesizer of the first embodiment of the present invention. The FDG synthesizer of the first embodiment of the present invention comprises a labeling reaction resin column 25 for trapping an [$^{18}$F] fluoride ion contained in target water, and then performing a labeling reaction between the thus trapped [$^{18}$F] fluoride ion and triflate, on the one hand, and a hydrolysis reaction vessel 35 for receiving a reaction intermediate product obtained from the labeling reaction and performing a hydrolysis reaction, on the other hand. In FIG. 2, 21 is a target box for producing an O-18 ($^{18}$O) water, i.e., target water, 42 is an ion retardation resin column, and 43 is a refining column. The labeling reaction resin column 25 comprises a column filled with a polymer-supported phase-transfer catalyst resin comprising a fixed phosphonium salt or a fixed pyridinium salt, which is obtained by fixing a phosphonium salt or a pyridinium salt to a polystyrene resin. The target water is passed through the labeling reaction resin column 25 to trap therein an [$^{18}$F] fluoride ion contained in the target water, and then, an acetonitrile aqueous solution is passed through the labeling reaction resin column 25, in which the [$^{18}$F] fluoride ion has been trapped, to dry the labeling reaction resin column 25. Then, a triflate solution is passed through the thus dried labeling reaction resin column 25 to perform a labeling reaction between the trapped [$^{18}$F] fluoride ion and triflate.

The O-18 ($^{18}$O) water, which has been passed through the labeling reaction resin column 25 and has been separated from the [$^{18}$F] fluoride ion trapped therein, is recovered into an O-18($^{18}$O) water recovery container 26 by the operation of a three-way valve 30. Then, the acetonitrile solution and the like used for drying the labeling reaction resin column 25 are recovered into a waste liquid recovery container 31 by the operation of three-way valves 30, 34. In the labeling reaction resin column 25, as described above, the [$^{18}$F] fluoride ion is trapped, and then, the labeling reaction is performed there. A special process for recovering the O-18 ($^{18}$O) water is not therefore required. Since moisture hinders the labeling reaction, on the other hand, moisture must be eliminated. However, by replacing the labeling reaction vessel with a column, it is possible to eliminate moisture in the column 25 only by passing the organic solvent through the column 25. Further, since the catalyst is fixed to the resin, a special process for separating and eliminating the catalyst is not required, and the labeling reaction efficiency is improved.

In the hydrolysis reaction vessel 35, there is performed a hydrolysis reaction for separating a protecting group (usually an acetyl group) from a reaction intermediate product labeled through the labeling reaction in the labeling reaction resin column 25. More specifically, an acetonitrile solution of triflate is passed through the labeling reaction resin column 25 having trapped the fluoride ion, to perform a labeling reaction of triflate in the labeling reaction resin column 25. Then, the solution containing the reaction intermediate product labeled through the labeling reaction, is received in the hydrolysis reaction vessel 35 in which the above-mentioned solution is then heated to evaporate acetonitrile. Then, a strong acidic aqueous solution or a strong alkaline aqueous solution such as a hydrochloric acid aqueous solution or a sodium hydroxide aqueous solution is added to the hydrolysis reaction vessel 35, and the hydrolysis reaction vessel 35 is heated to perform a hydrolysis reaction.

After the completion of the hydrolysis reaction, germfree water is added to a reaction product in the hydrolysis reaction vessel 35, and the reaction product is passed together with germfree water sequentially through the ion retardation resin column 42 and the refining column 43 to synthesize FDG. In the ion retardation resin column 42, unnecessary hydrochloric acid aqueous solution or sodium hydroxide aqueous solution is eliminated. In the refining column 23, FDG is further refined.

A target water container 22, an acetonitrile container 28 and a triflate container 32 communicate with the labeling reaction resin column 25 through syringes 23, 27 and three-way valves 24, 29, 33. Further, the O-18($^{18}$O) water recovery container 26 and the waste liquid recovery container 31 communicate with the labeling reaction resin column 25 through the three-way valves 30, 34. The labeling reaction resin column 25 communicates with the hydrolysis reaction vessel 35 through the three-way valves 30, 34. A germfree water container 39 and a hydrochloric acid aqueous solution container 36 communicate with the hydrolysis reaction vessel 35 through a syringe 37 and three-way valves 41, 38. Further, the ion retardation resin column 42 and the refining column 43 communicate with the hydrolysis reaction vessel 35 through a three-way valve 40.

Figure 3:
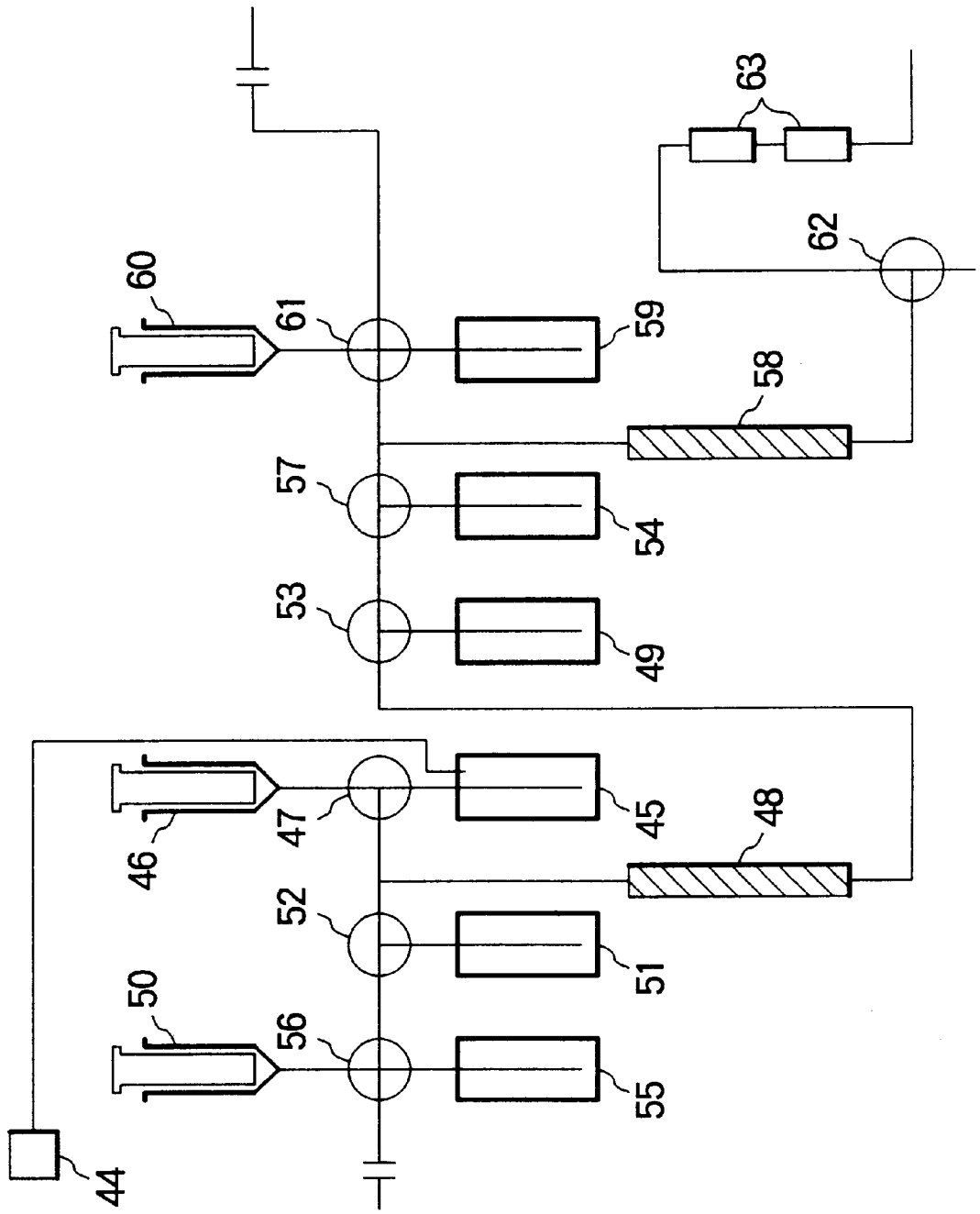
FIG. 3 is a schematic descriptive view illustrating an FDG synthesizer of a second embodiment of the present invention.

FIG. 3 is a schematic descriptive view illustrating the FDG synthesizer of the second embodiment of the present invention. The FDG synthesizer of the second embodiment of the invention comprises a labeling reaction resin column 48 for trapping an [$^{18}$F] fluoride ion contained in a target water, and then performing a labeling reaction between the thus trapped [$^{18}$F] fluoride ion and triflate, on the one hand, and a cation-exchange resin column 58 for bringing a reaction intermediate product obtained from the labeling reaction into contact with a cation-exchange resin adjusted to an H$^+$ type and heating same for a hydrolysis reaction, on the other hand. In FIG. 3, 44 is a target box for producing an O-18($^{18}$O) water, i.e., a target water, and 63 is a refining column.

The labeling reaction resin column 48 comprises a column filled with a polymer-supported phase-transfer catalyst resin comprising a fixed phosphonium salt or a fixed pyridinium salt, which is obtained by fixing a phosphonium salt or a pyridinium salt to a polystyrene resin. As in the first embodiment of the present invention, the target water is passed through the labeling reaction resin column 48 to trap therein an [$^{18}$F] fluoride ion contained in the target water, and then, an acetonitrile aqueous solution is passed through the labeling reaction resin column 48, in which the [$^{18}$F] fluoride ion has been trapped, to dry the labeling reaction resin column 48. Then, a triflate solution is passed through the thus dried labeling reaction resin column 48 to perform a labeling reaction between the trapped [$^{18}$F] fluoride ion and triflate.

The O-18($^{18}$O) water, which has been passed through the labeling reaction resin column 48 and has been separated from the [$^{18}$F] fluoride ion trapped therein, is recovered into an O-18($^{18}$O) water recovery container 49 by the operation of a three-way valve 53. Then,.the acetonitrile solution and the like used for drying the labeling reaction resin column 48 are recovered into a waste liquid recovery container 54 by the operation of three-way valves 53, 57. In the labeling reaction resin column 48, as described above, the [$^{18}$F] fluoride ion is trapped, and then, the labeling reaction is performed there. A special process for recovering the O-18 (180) water is not therefore required. Since moisture hinders the labeling reaction, on the other hand, it is necessary to eliminate moisture. However, by replacing the labeling reaction vessel with a column, it is possible to eliminate moisture in the column 48 only by passing the organic solvent through the column 48. Further, since the catalyst is fixed onto the resin, a special process for separating and eliminating the catalyst is not required, and the labeling reaction efficiency is improved.

In the cation-exchange resin column 58, a hydrolysis reaction is performed for separating a protecting group (usually, an acetyl group) from a reaction intermediate product labeled through the labeling reaction in the labeling reaction resin column 48. More specifically, an acetonitrile solution of triflate is passed through the labeling reaction resin column 48 having trapped the [$^{18}$F] fluoride ion, to perform a labeling reaction of triflate in the labeling reaction resin column 48. Then, the solution containing the reaction intermediate product labeled through the labeling reaction, is passed through the cation-exchange resin column 58, in which the above-mentioned solution is brought into contact with the cation-exchange resin adjusted to an H$^+$ type, and, at the same time, acetonitrile is evaporation-eliminated. Then, the cation-exchange resin column 58 is heated at a temperature of about 130° C. for 10 to 15 minutes to perform a hydrolysis reaction. In the second embodiment, unlike the first embodiment, the use of a hydrochloric acid aqueous solution or a sodium hydroxide aqueous solution is not required upon the hydrolysis reaction, thus making it unnecessary to use an ion retardation resin for eliminating such an aqueous solution or a reagent for neutralizing the same, and a reaction vessel becomes unnecessary.

After the completion of the hydrolysis reaction, germfree water is added to the reaction product in the cation-exchange resin column 58, and the reaction product is passed together with the germfree water through the refining column 63 to synthesize FDG. It is thus possible to obtain FDG in the germfree water through a simple operation of only passing the reaction product together with the germfree water through the cation-exchange resin column 58 after the hydrolysis.

A target water container 45, an acetonitrile container 51 and a triflate container 55 communicate with the labeling reaction resin column 48 through syringes 46, 50 and three-way valves 47, 52, 56. Further, the O-18($^{18}$O) water recovery container 49 and the waste liquid recovery container 54 are communicated with the labeling reaction resin column 48 through the three-way valves 53, 57. The labeling reaction resin column 48 communicates with the cation-exchange resin column 58 through the three-way valves 53, 57. A germfree water container 59 communicates with the cation-exchange resin column 58 through a syringe 60 and a three-way valve 61. Further, the refining column 63 communicates with the cation-exchange resin column 58 through a three-way valve 62.

Figure 4:
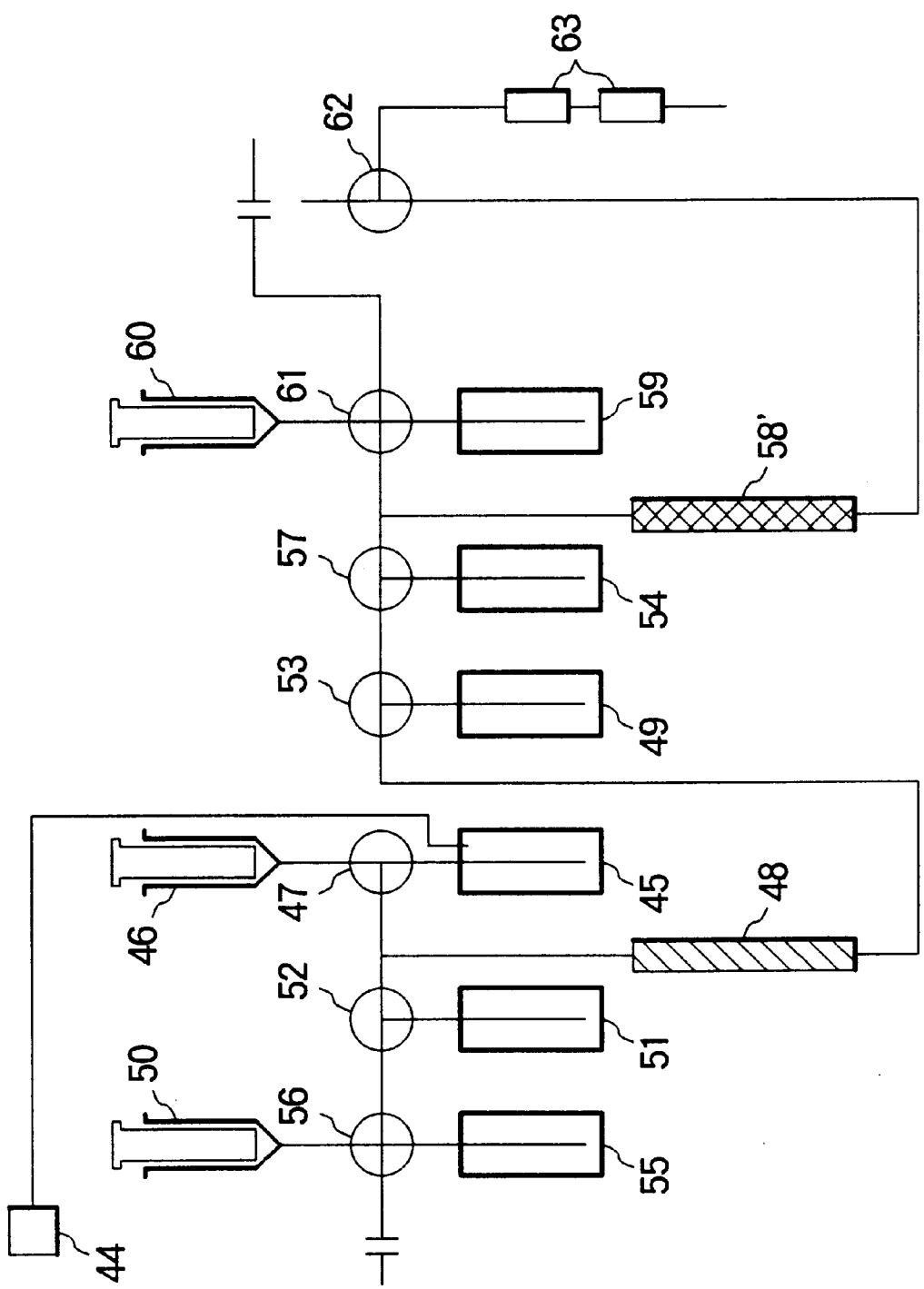
FIG. 4 is a schematic descriptive view illustrating an FDG synthesizer of a third embodiment of the present invention.

FIG. 4 is a schematic perspective view illustrating the FDG synthesizer of the third embodiment of the present invention. The FDG synthesizer of the third embodiment of the present invention comprises a labeling reaction resin column 48 for trapping an [$^{18}$F] fluoride ion contained in a target water, and then performing a labeling reaction between the thus trapped [$^{18}$F] fluoride ion and triflate, on the one hand, and a cation-exchange resin column 58' for heating a reaction intermediate product containing an organic solvent obtained from the labeling reaction, to evaporation-eliminate the organic solvent, and at the same time, bringing the reaction intermediate product after the elimination of the organic solvent into contact with a cation-exchange resin adjusted to an H$^+$ type, to perform a hydrolysis reaction, on the other hand.

In the cation-exchange resin column 58' of the third embodiment of the present invention, the reaction intermediate product of FDG from which the organic solvent has been evaporation-eliminated in the column 58', is brought into contact with the cation-exchange resin in the column 58', by increasing the amount of evaporation per unit time of an organic solvent passing through the column 58' larger than the flow rate per unit time of an organic solvent flowing anew into the column 58', through the adjustment of the flow rate of the reaction intermediate product containing the organic solvent, passing through the column 58', and the temperature in the column 58'.

The cation-exchange resin column 58' has a heating means (not shown) for adjusting the temperature in the column 58' and a flow rate control means (not shown) for controlling the flow rate of a reaction intermediate product containing an organic solvent. It is possible to increase the amount of evaporation per unit time of an organic solvent passing through the column 58' larger than the flow rate per unit time of an organic solvent flowing anew into the column 58', by adjusting the temperature in the column 58' within a range of from 90 to 150° C. with the use of the heating means, and by controlling the flow rate of the reaction intermediate product containing the organic solvent within a range of from 0.5 to 1.5 cc/minute with the use of the flow rate control means.

A cation-exchange resin containing moisture or a dried cation-exchange resin may be used for the cation-exchange resin column 58' of the third embodiment of the present invention. When using a cation-exchange resin containing moisture, it is desirable to use the cation-exchange resin in a sufficient amount. When using a dried cation-exchange resin, it is possible to achieve an effective hydrolysis reaction with the use of the dried cation-exchange resin in a slight amount, because of the easy separation of the reaction intermediate product from the organic solvent. When using a dried cation-exchange resin, it is necessary to add water upon the hydrolysis reaction.

In FIG. 4, 44 is a target box for producing an O-18($^{18}$O) water, i.e., a target water, and 63 is a refining column. The labeling reaction resin column 48 comprises a column filled with a polymer-supported phase-transfer catalyst resin comprising a fixed phosphonium salt or a fixed pyridinium salt, which is obtained by fixing a phosphonium salt or pyridinium salt to a polystyrene resin. As in the first embodiment of the present invention, the target water is passed through the labeling reaction resin column 48 to trap therein an [$^{18}$F] fluoride ion contained in the target water, and then, an acetonitrile aqueous solution is passed through the labeling reaction resin column 48, in which the [$^{18}$F] fluoride ion has been trapped, to dry the column 48. Then, a triflate solution is passed through the thus dried labeling reaction resin column 48 to perform a labeling reaction between the trapped [$^{18}$F] fluoride ion and triflate.

The O-18($^{18}$O) water, which has been passed through the labeling reaction resin column 48 and has been separated from the [$^{18}$F] fluoride ion trapped therein, is received into an O-18($^{18}$O) water recovery container 49 by the operation of a three-way valve 53. Then, the acetonitrile solution and the like used for drying the labeling reaction resin column 48 are recovered into a waste liquid recovery container 54 by the operation of three-way valves 53, 57. In the labeling reaction resin column 48, as described above, the [$^{18}$F] fluoride ion is trapped, and then, the labeling reaction is performed there. A special process for recovering the O-18 ($^{18}$O) water is not therefore required. Since moisture hinders the labeling reaction, on the other hand, it is necessary to eliminate moisture. By replacing the labeling reaction vessel with a column, however, it is possible to eliminate moisture in the column 48 only by passing the organic solvent through the column 48. Further, since the catalyst is fixed to the resin, a special process for separating and eliminating the catalyst is not required, and the labeling reaction efficiency is improved.

In the cation-exchange resin column 58', a hydrolysis reaction is performed for separating a protecting group (usually, an acetyl group) from a reaction intermediate product labeled through the labeling reaction in the labeling reaction resin column 48. More specifically, an organic solvent (acetonitrile) is evaporation-eliminated by passing the reaction intermediate product containing the organic solvent at a flow rate within a range of from 0.5 to 1.5 cc/minute through the cation-exchange resin column 58' with the use of the flow rate control means (not shown), and at the same time, the reaction intermediate product after the elimination of the organic solvent is heated at a temperature of about 130° C. for 10 to 15 minutes, while bringing the same into contact with the cation-exchange resin adjusted to an H$^+$ type, to perform a hydrolysis reaction. It is therefore possible to prevent the reaction intermediate product produced in the labeling reaction from flowing out together with the organic solution from the cation-exchange resin column 58' without being trapped by the column 58'. Furthermore, since the use of a hydrochloric acid aqueous solution or a sodium hydroxide aqueous solution is not required upon the hydrolysis reaction, it is not necessary to use an ion retardation resin for eliminating such an aqueous solution or a reagent for neutralizing the same, and a reaction vessel becomes unnecessary. According to the FDG synthesizer of the third embodiment of the present invention, it is possible to perform the elimination of the organic solvent upon the passing of the reaction intermediate product through the cation-exchange resin column 58', and then, to perform a hydrolysis reaction in the column 58'.

After the completion of the hydrolysis reaction, germfree water is added to the reaction product in the cation-exchange resin column 58', and the reaction product is passed together with the germfree water through the refining column 63 to synthesize FDG. It is thus possible to obtain FDG in the germfree water through a simple operation of only passing the reaction product together with the germfree water through the cation-exchange resin column 58' after the hydrolysis.

As in the second embodiment, a target water container 45, an acetonitrile container 51 and a triflate container 55 are communicated with the labeling reaction resin column 48 through syringes 46, 50 and three-way valves 47, 52, 56. Further, the O-18($^{18}$O) water recovery container 49 and the waste liquid recovery container 54 communicate with the labeling reaction resin column 48 through three-way valves 53, 57. The labeling reaction resin column 48 communicates with the cation-exchange resin column 58' through the three-way valves 53, 57. A germfree water container 59 communicates with the cation-exchange resin column 58' through a syringe 60 and a three-way valve 61. Further, the refining column 63 communicates with the cation-exchange resin column 58' through a three-way valve 62.

Figure 5:
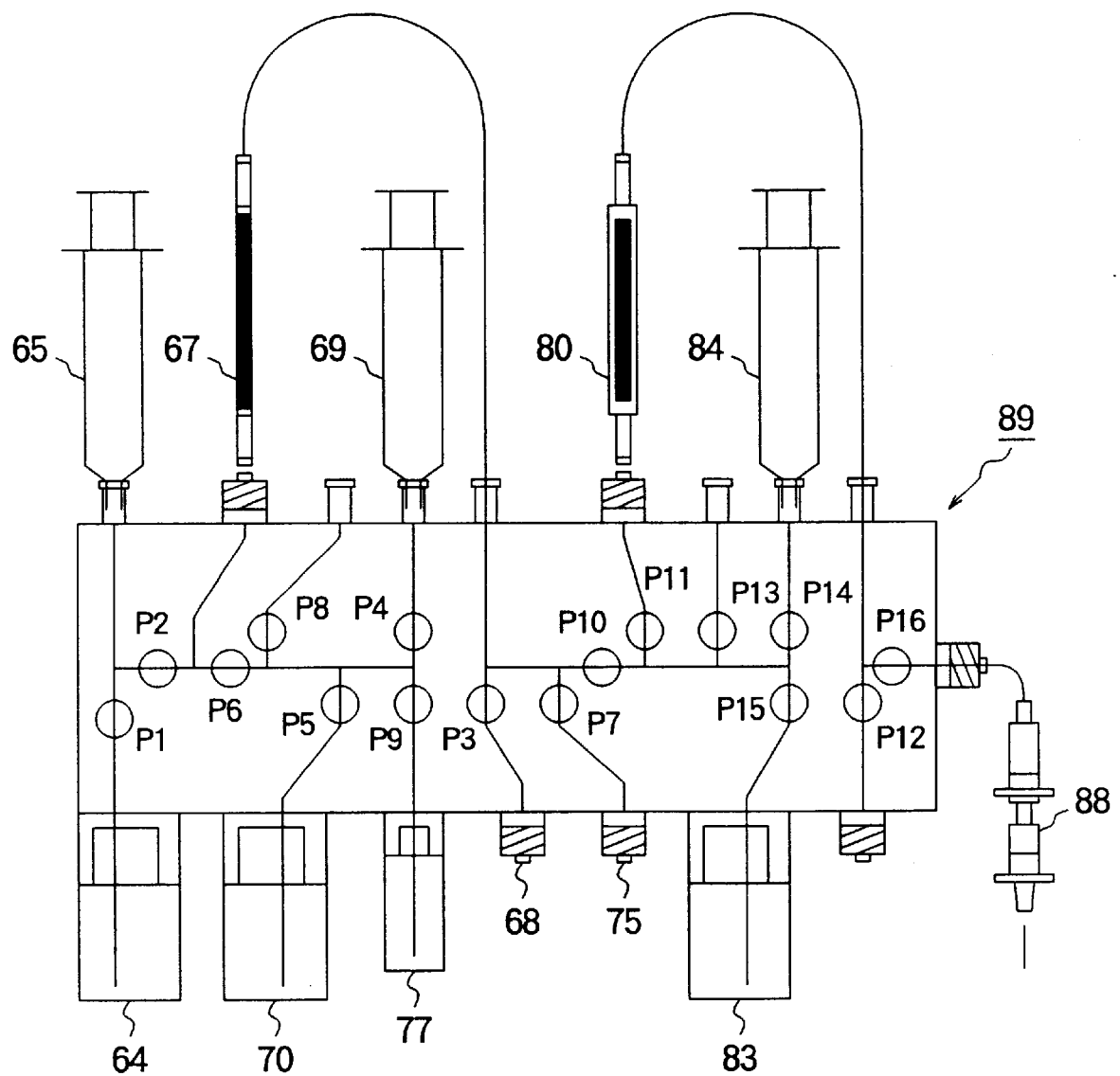
FIG. 5 is a schematic descriptive view illustrating an FDG synthesizer of a fourth embodiment of the present invention.

FIG. 5 is a schematic descriptive view illustrating the FDG synthesizer of the fourth embodiment of the present invention. The FDG synthesizer of the fourth embodiment of the present invention comprises (a) a cartridge-type labeling reaction resin column 67, (b) a cartridge-type cation-exchange resin column 80, and (c) a disposable cartridge base 89 into which paths and switchover valves for communicating the labeling reaction resin column 67 and the cation-exchange resin column 80 are incorporated. The above-mentioned FDG synthesizer of the fourth embodiment of the present invention is one-touch-attachable to a synthesizer body (not shown) comprising a driving means for driving the switchover valves, a syringe driving means for driving syringes, a heating means for heating the columns 67, 80, and a gas supply means for transferring liquid and for drying the columns 67, 80. In FIG. 5, P1 to P16 are pinch valves.

The cartridge-type cation-exchange resin column 80 is disposable, and one-touch-releasably attachable to the cartridge base 89. In the cartridge-type cation-exchange resin column 80, a reaction intermediate product of FDG from which an organic solvent has been evaporation-eliminated in the column 80, is brought into contact with the cation-exchange resin in the column 80, by increasing the amount of evaporation per unit time of an organic solvent passing through the column 80 larger than the flow rate per unit time of an organic solvent flowing anew into the column 80, through the adjustment of the flow rate of the reaction intermediate product containing the organic solvent, passing through the column 80, and the temperature in the column 80.

The cation-exchange resin column 80 has a heating means (not shown) for adjusting the temperature in the column 80, and a flow rate control means (not shown) for controlling the flow rate of a reaction intermediate product containing an organic solvent. It is possible to increase the amount of evaporation per unit time of an organic solvent passing through the column 80 larger than the flow rate per unit time of an organic solvent flowing anew into the column 80, by adjusting the temperature in the column 80 within a range of from 90 to 150° C. with the use of the heating means, and by controlling the flow rate of the reaction intermediate product containing the organic solvent within a range of from 0.5 to 1.5 cc/minute with the use of the flow rate control means.

As in the third embodiment, a cation-exchange resin containing moisture or a dried cation-exchange resin may be used for the cation-exchange resin column 80 in the fourth embodiment of the present invention. When using a cation-exchange resin containing moisture, it is desirable to use the moisture-containing cation-exchange resin in a sufficient amount. When using a dried cation-exchange resin, it is possible to achieve an effective hydrolysis reaction with the use of the dried cation-exchange resin in a slight amount, because of the easy separation of the reaction intermediate product from the organic solvent. When using a dried cation-exchange resin, it is necessary to add water upon hydrolysis reaction.

The cartridge-type labeling reaction resin column 67 is disposable and one-touch-releasably attachable to the cartridge base 89. The cartridge-type labeling reaction resin column 67 comprises a column filled with a polymer-supported phase-transfer catalyst resin comprising a fixed phosphonium salt or a fixed pyridinium salt, which is obtained by fixing a phosphonium salt or a pyridinium salt to a polystyrene resin. As in the first embodiment of the present invention, the target water is passed through the labeling reaction resin column 67 to trap therein an [$^{18}$F] fluoride ion contained in the target water, and then, an acetonitrile aqueous solution is passed through the labeling reaction resin column 67, in which the [$^{18}$F] fluoride ion has been trapped, to dry the column 67. Then, a triflate solution is passed through the thus dried labeling reaction resin column 67 to perform a labeling reaction between the trapped [$^{18}$F] fluoride ion and triflate.

The O-18($^{18}$O) water, which has been passed through the labeling reaction resin column 67 and has been separated from the [$^{18}$F] fluoride ion trapped therein, is recovered into an O-18($^{18}$O) water recovery container (not shown) connected to a connector 68 by the operation of the pinch valves P3, P7, P10. Then, the acetonitrile solution and the like used for drying the labeling reaction resin column 67 are recovered into a waste liquid recovery container (not shown) connected to a connector 75 by the operation of the pinch valves P3, P7, P10. In the labeling reaction resin column 67, as described above, the [$^{18}$F] fluoride ion is trapped, and then the labeling reaction is performed there. A special process for recovering the O-18($^{18}$O) water is not therefore required. Since moisture hinders the labeling reaction, on the other hand, it is necessary to eliminate moisture. By replacing the reaction vessel with a column, however, it is possible to eliminate moisture in the column 67 only by passing the organic solvent through the column 67. Further, since the catalyst is fixed to the resin, a special process for separating and eliminating the catalyst is not required, and the labeling reaction efficiency is improved. Furthermore, since the labeling reaction resin column 67 is of the cartridge type, it is possible to easily make a replacement and a setup thereof, and to prevent fluctuations of the synthesizing yield and quality of FDG.

In the cartridge-type cation-exchange resin column. 80, a hydrolysis reaction is performed for separating a protecting group (usually, an acetyl group) from a reaction intermediate product labeled through the labeling reaction in the labeling reaction resin column 67. More specifically, a triflate solution is passed through the labeling reaction resin column 67 in which the [$^{18}$F] fluoride ion has been trapped, and then, the solution produced by the labeling reaction is brought into contact a cation-exchange resin adjusted to an H$^+$ type, and, at the same time, acetonitrile is evaporated, and then, a hydrolysis reaction is performed at a temperature of about 130° C. for 10 to 15 minutes. In the cartridge-type cation-exchange resin column 80, as described above, a reaction intermediate product of FDG from which an organic solvent has been evaporation-eliminated in the column 80, is brought into contact with the cation-exchange resin in the column 80, by increasing the amount of evaporation per unit time of an organic solvent passing through the column 80 larger than the flow rate per unit time of an organic solvent flowing anew into the column 80, through the adjustment of the flow rate of the reaction intermediate product containing the organic solvent, passing through the column 80, and temperature in the column 80. Therefore, since the use of a hydrochloric acid aqueous solution or a sodium hydroxide aqueous solution is not required upon the hydrolysis reaction, it is not necessary to use an ion retardation resin for eliminating such an aqueous solution or a reagent for neutralizing the same, and a reaction vessel becomes unnecessary. Further, because the cation-exchange resin column 80 is of the cartridge type, it is possible to easily make a replacement and a setup thereof, and to prevent fluctuations of the synthesizing yield and quality of FDG.

After the completion of the hydrolysis reaction, germfree water is added to the reaction product in the cation-exchange resin column 80, and the reaction product is passed together with the germfree water through a refining column 88 to synthesize FDG. It is thus possible to obtain FDG in the germfree water through a simple operation of only passing the reaction product together with the germfree water through the cation-exchange resin column 80 after the hydrolysis.

A target water container 64, an acetonitrile container 70, a triflate container 77, a germfree water container 83 and syringes 65, 69, 84 are attached to the cartridge base 89. Connectors of the individual cartridge-type columns can be easily attached to and detached from the cartridge base 89. For example, a Luer-type connector is preferable. Paths communicating between two pinch valves or between a pinch valve and a connector comprise a teflon tube or a polypropylene tube. These paths may be formed by directly piercing throughholes in the cartridge base 89 itself.

Figure 6:
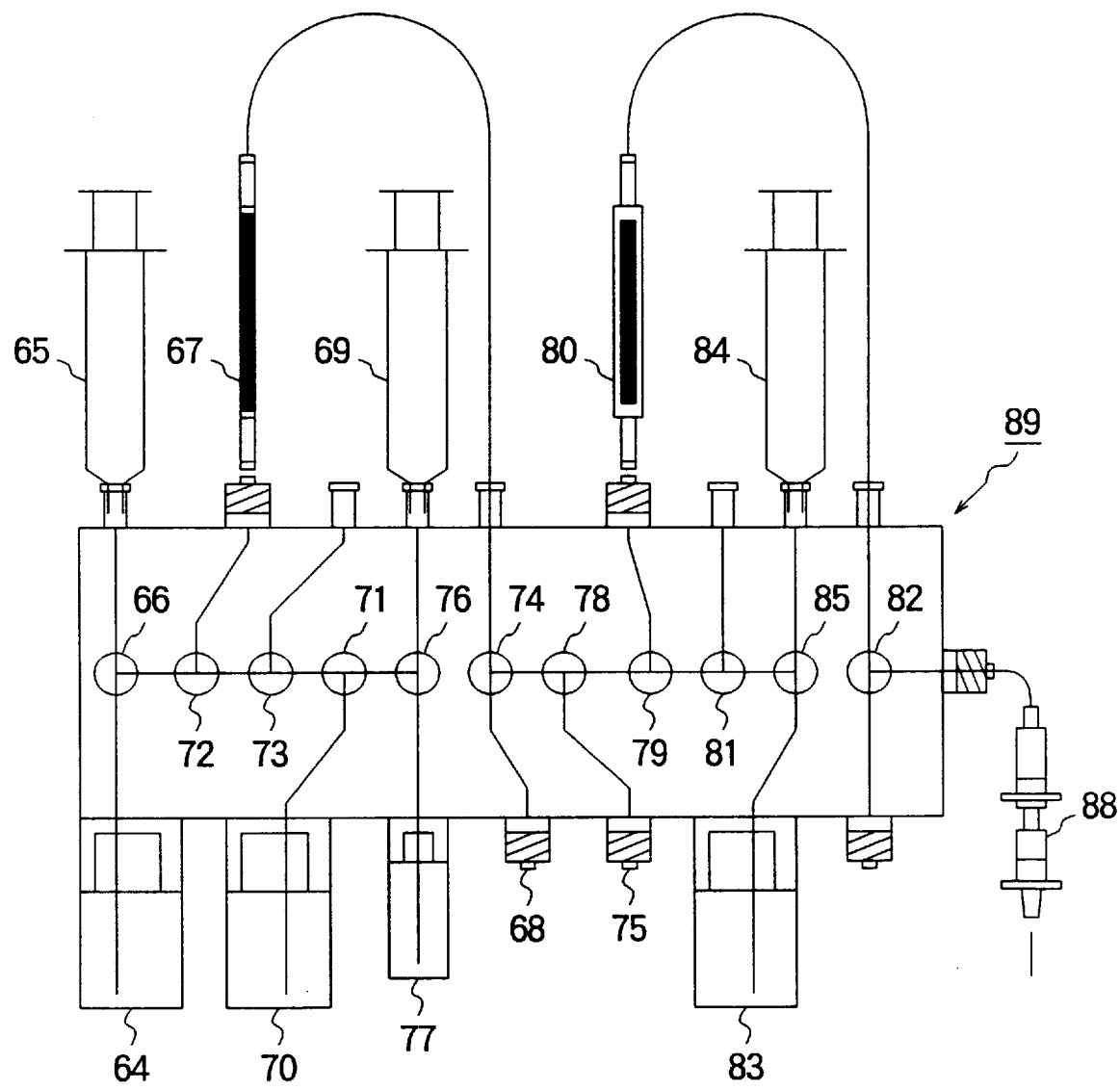
FIG. 6 is a schematic descriptive view illustrating an FDG synthesizer of a fifth embodiment of the present invention.

FIG. 6 is a schematic descriptive view illustrating the FDG synthesizer of the fifth embodiment of the present invention. The FDG synthesizer of the fifth embodiment of the present invention comprises (a) a cartridge-type labeling reaction resin column 67, (b) a cartridge-type cation-exchange resin column 80, and (c) a disposable cartridge base 89 into which paths and switchover valves for communicating the labeling reaction resin column 67 and the cation-exchange resin column 80 are incorporated. The above-mentioned FDG synthesizer of the fifth embodiment of the present invention is one-touch-attachable to a synthesizer body (not shown) comprising a driving means for driving the switchover valves, a syringe driving means for driving syringes, a heating means for heating the columns 67, 80, and a gas supply means for transferring liquid and for drying the columns 67, 80. In FIG. 6, 66, 71 to 74, 76, 78, 79, 81, 82 and 85 are three-way valves each incorporating a three-way switchover cock therein.

The FDG synthesizer of the fifth embodiment differs from the FDG synthesizer of the fourth embodiment described above in that three-way valves are used in the fifth embodiment, whereas pinch valves are used in the fourth embodiment.

As in the fourth embodiment, the cartridge-type cation-exchange resin column 80 of the fifth embodiment of the present invention is disposable, and one-touch-attachable to the cartridge base 89. In the cartridge-type cation-exchange resin column 80, a reaction intermediate product of FDG from which an organic solvent has been evaporation-eliminated in the column 80, is brought into contact with the cation-exchange resin in the column 80, by increasing the amount of evaporation per unit time of an organic solvent passing through the column 80 larger than the flow rate per unit time of an organic solvent flowing anew into the column 80, through the adjustment of the flow rate of the reaction intermediate product containing the organic solvent, passing through the column 80, and the temperature in the column 80.

As in the fourth embodiment, the cation-exchange resin column 80 has a heating means (not shown) for adjusting the temperature in the column 80, and a flow rate control means (not shown) for controlling the flow rate of a reaction intermediate product containing an organic solvent. It is possible to increase the amount of evaporation per unit time of an organic solvent passing through the column 80 larger than the flow rate per unit time of an organic solvent flowing anew into the column 80, by adjusting the temperature in the column 80 within a range of from 90 to 150° C. with the use of the heating means, and by controlling the flow rate of the reaction intermediate product containing the organic solvent within a range of from 0.5 to 1.5 cc/minute with the use of the flow rate control means.

As in the third embodiment, a cation-exchange resin containing moisture or a dried cation-exchange resin may be used for the cation-exchange resin column 80 in the fifth embodiment of the present invention. When using a cation-exchange resin containing moisture, it is desirable to use the moisture-containing cation-exchange resin in a sufficient amount. When using a dried cation-exchange resin, it is possible to achieve an effective hydrolysis reaction with the use of the dried cation-exchange resin in a slight amount, because of the easy separation of the reaction intermediate product from the organic solvent. When using a dried cation-exchange resin, it is necessary to add water upon hydrolysis reaction.

The cartridge-type labeling reaction resin column 67 is disposable and one-touch-releasably attachable to the cartridge base 89. The cartridge-type labeling reaction resin column 67 comprises a column filled with a polymer-supported phase-transfer catalyst resin comprising a fixed phosphonium salt or a fixed pyridinium salt, which is obtained by fixing a phosphonium salt or a pyridinium salt to a polystyrene resin. As in the first embodiment of the present invention, the target water is passed through the labeling reaction resin column 67 to trap an [$^{18}$F] fluoride ion contained in the target water, and then, an acetonitrile aqueous solution is passed through the labeling reaction resin column 67, in which the [$^{18}$F] fluoride ion has been trapped, to dry the column 68. Then, a triflate solution is passed through the thus dried labeling reaction resin column 67 to perform a labeling reaction between the trapped [$^{18}$F] fluoride ion and triflate.

The O-18($^{18}$O) water, which has been passed through the labeling reaction resin column 67 and has been separated from the [$^{18}$F] fluoride ion trapped therein, is recovered into an O-18($^{18}$O) water recovery container (not shown) connected to a connector 68 by the operation of the three-way valve 74. Then, the acetonitrile solution and the like used for drying the labeling reaction resin column 67 are recovered into a waste liquid recovery container (not shown) connected to a container 75 by the operation of the three-way valves 74, 78. In the labeling reaction resin column 67, as described above, the [$^{18}$F] fluoride ion is trapped, and then, the labeling reaction is performed there. A special process for recovering the O-18($^{18}$O) water is not therefore required. Since moisture hinders the labeling reaction, on the other hand, it is necessary to eliminate moisture. By replacing the reaction vessel with a column, however, it is possible to eliminate moisture in the column 67 only by passing the organic solvent through the column 67. Further, since the catalyst is fixed to the resin, a special process for separating and eliminating the catalyst is not required, and the labeling reaction efficiency is improved. Furthermore, since the labeling reaction resin column 67 is of the cartridge type, it is possible to easily make a replacement and a setup thereof, and to prevent fluctuations of the synthesizing yield and quality of FDG.

In the cartridge-type cation-exchange resin column 80, a hydrolysis reaction is performed for separating a protecting group (usually, an acetyl group) from a reaction intermediate product labeled through the labeling reaction in the labeling reaction resin column 67 is performed. More specifically, a triflate solution is passed through the labeling reaction resin column 67 in which the [$^{18}$F] fluoride ion has been trapped, and then, the solution produced by the labeling reaction is brought into contact with a cation-exchange resin adjusted to an H$^+$ type, and at the same time, acetonitrile is evaporated, and then, a hydrolysis reaction is performed at a temperature of about 130° C. for 10 to 15 minutes. In the cartridge-type cation-exchange resin column 80, as described above, a reaction intermediate product of FDG from which an organic solvent has been evaporation-eliminated in the column 80, is brought into contact with the cation-exchange resin in the column 80, by increasing the amount of evaporation per unit time of an organic solvent passing through the column 80 larger than the flow rate per unit time of an organic solvent flowing anew into the column 80, through the adjustment of the flow rate of the reaction intermediate product containing the organic solvent, passing through the column 80, and temperature in the column 80. Therefore, since the use of a hydrochloric acid aqueous solution or a sodium hydroxide aqueous solution is not required upon the hydrolysis reaction, it is not necessary to use an ion retardation resin for eliminating such an aqueous solution or a reagent for neutralization of the same, and a reaction vessel becomes unnecessary. Further, because the cation-exchange resin column 80 is of the cartridge type, it is possible to easily make a replacement and a setup thereof, and to prevent fluctuations of the synthesis product yield and quality of FDG.

After the completion of the hydrolysis reaction, as in the fourth embodiment, germfree water is added to the reaction product in the cation-exchange resin column 80, and the reaction product is passed together with the germfree water through a refining column 88 to synthesize FDG. It is thus possible to obtain FDG in the germfree water through a simple operation of only passing the reaction product together with the germfree water through the cation-exchange resin column 80 after the hydrolysis.

A target water container 64, an acetonitrile container 70, a triflate container 77, a germfree water container 83 and syringes 65, 69, 84 are attached to the cartridge base 89. Connectors of the individual cartridge-type columns can be easily attached to and detached from the cartridge base 89. For example, a Luer-type connector is preferable. Paths communicating between two three-way valves or between a three-way valve and a connector comprise a teflon tube or a polypropylene tube. These paths may be formed by directly piercing throughholes in the cartridge base 89 itself.

The FDG synthesizer of the present invention is described further in detail by means of examples.

EXAMPLE 1

A labeling reaction resin column 25 (refer to FIG. 2) of the first embodiment of the present invention was formed by filling a stainless steel cylinder having an inside diameter of 2 mm and a length of 5 cm with a slurry-like mixture which was prepared by mixing 100 to 200 mesh resin powder with a mixed solvent of ethanol and water.

As shown in FIG. 2, a target water, i.e., an irradiated O-18($^{18}$O) water containing an [$^{18}$F] fluoride ion was sent from a target box 21 to a target water container 22. Then, the target water was sucked up from the target water container 22 by means of a syringe 23, by switching over a three-way valve 24, and then, the thus sucked up target water was sent to the labeling reaction resin column 25 heated to a temperature within a range of from 80 to 100° C. by switching over three-way valves 24 and 29. The [$^{18}$F] fluoride ion was trapped into the resin in the labeling reaction resin column 25, and at the same time, the O-18($^{18}$O) water was separated. Then, the separated O-18($^{18}$O) water was sent to an O-18 ($^{18}$O) water recovery container 26, by switching over a three-way valve 30. Then, acetonitrile was sucked up from an acetonitrile container 28 by means of a syringe 27, by switching over three-way valves 29, 33, and then, the thus sucked up acetonitrile was passed through the labeling reaction resin column 25 by switching over the three-way valves 24, 29, to dry the labeling reaction resin column 25. Then, the used acetonitrile was discharged into a waste liquid recovery container 31, by switching over the three-way valves 30, 34.

Then, a triflate solution was sucked up from a triflate container 32 by means of a syringe 27 by switching over the three-way valve 33, and then, the thus sucked up triflate solution was passed through the labeling reaction resin column 25, by switching over the three-way valves 24, 29, 33, to perform a labeling reaction of triflate in the labeling reaction resin column 25. Then, the solution containing the reaction intermediate product was sent to a hydrolysis reaction vessel 35, by switching over three-way valves 30, 34, 41. Then, the hydrolysis reaction vessel 35 was heated to evaporate acetonitrile, and then, a hydrochloric acid aqueous solution was sucked up from a hydrochloric acid aqueous solution container 36 by means of a syringe 37, by switching over a three-way valve 38, and then, the thus sucked up hydrochloric aqueous acid solution was sent to the hydrolysis reaction vessel 35, by switching over the three-way valves 38, 41, 34. Then, the hydrolysis reaction vessel 35 was heated to a temperature of about 130° C. for 10 to 15 minutes to perform a hydrolysis reaction.

After the hydrolysis reaction, germfree water was sucked up from a germfree water container 39 by means of the syringe 37, by switching over the three-way valves 38, 41, and then, the thus sucked up germfree water was sent to the hydrolysis reaction vessel 35, by switching over the three-way valves 38, 41, 34. Then, the reaction product was passed, together with the germfree water, sequentially through an ion retardation resin column 42 and a refining column 43, by switching over a three-way valve 40, to obtain FDG.

Results of sythesis of FDG according to the FDG synthesizer of the first embodiment of the present invention are shown in Tables 1 and 2.

TABLE 1

| | FDG synthesizer of the prior art | | | FDG synthesizer of the invention | |
|---|---|---|---|---|---|
| No. | Operation | Time (min:sec) | No. | Operation | Time (min:sec) |
| 1 | Recovery of 0–18 ($^{18}$O) water | 1:38 | 1 | Recovery of 0–18 ($^{18}$O) water | 1:38 |
| 2 | Addition of K$_2$CO$_3$ | 0:47 | | | |
| 3 | Addition of kryptofix 222 | 0:32 0:32 | | | |
| 4 | Evaporation -1 | 3:30 | 2 | Evaporation (Addition of CH$_3$CN) | 3:00 |
| 5 | Addition of acetonitrile | 0:35 | | | |
| 6 | Evaporation -2 | 1:45 | | | |
| 7 | Addition of triflate | 0:56 | | | |
| 8 | Labeling reaction | 5:00 | 3 | Labeling reaction | 1:00 |
| 9 | Addition of water | 0:49 | | | |
| 10 | Collection of SepPak | 1:09 | | | |
| 11 | Addition of water | 0:49 | | | |
| 12 | Washing of SepPak | 1:10 | | | |
| 13 | Extraction of SepPak | 1:22 | | | |
| 14 | Concentration | 2:36 | 4 | Concentration | 2:36 |
| 15 | Addition of hydrochloric acid | 0:35 | 5 | Addition of hydrochloric acid | 0:35 |
| 16 | Hydrolysis reaction | 10:00 | 6 | Hydrolysis reaction | 10:00 |
| 17 | Elimination of hydrochloric acid | 2:00 | 7 | Elimination of hydrochloric acid | 2:00 |
| 18 | Refining | 1:15 | 8 | Refining | 1:15 |
| | Total time required | 36:28 | | Total time required | 22:04 |

TABLE 2

|  | FDG synthesizer of the prior art | FDG synthesizer of the invention |
| --- | --- | --- |
| Yield rate of labeling reaction product | about 30–70% | about 80% |
| Total time required for FDG synthesis | about 45 minutes | about 25 minutes |
| Yield rate of FDG synthesis product | about 23–54% | about 69% |

According to the FDG synthesizer of the first embodiment of the present invention, as is clear from Table 1, the FDG synthesizing process can be simplified to about half that of the prior art, and the total time required for FDG synthesis is largely reduced. Further, according to the FDG synthesizer of the first embodiment of the present invention, as is clear from Table 2, the FDG synthesis can be performed in a shorter period of time and a higher yield rate of the FDG synthesis product is achieved, as compared with the prior art.

EXAMPLE 2

A labeling reaction resin column 48 (refer to FIG. 3) of the second embodiment of the present invention was formed, in the same manner as in the Example 1, by filling a stainless steel cylinder having an inside diameter of 2 mm and a length of 5 cm with a slurry-like mixture which was prepared by mixing 100 to 200 mesh resin powder with a mixed solvent of ethanol and water. A cation-exchange resin column 58 (refer to FIG. 3) of the second embodiment of the present invention was formed, by filling a stainless steel cylinder having an inside diameter of 12 mm and a length of 4 cm with a cation-exchange resin adjusted to an $H^+$ type.

As shown in FIG. 3, a target water, i.e., an irradiated O-18($^{18}$O) water containing an fluoride ion was sent from a target box 44 to a target water container 45. Then, the target water was sucked up from the target water container 45 by means of a syringe 46, by switching over a three-way valve 47, and then, the thus sucked up target water was sent to the labeling reaction resin column 48 heated to a temperature within a range of from 80 to 100° C. by switching over the three-way valves 47, 52. The [$^{18}$F] fluoride ion was trapped into the resin in the labeling reaction resin column 48, and at the same time, the O-18($^{18}$O) water was separated. Then, the separated O-18($^{18}$O) water was sent to an O-18($^{18}$O) water recovery container 49, by switching over a three-way valve 53. Then, acetonitrile was sucked up from an acetonitrile container 51 by means of a syringe 50, by switching over the three-way valves 52, 56, and then, the thus sucked up acetonitrile was passed through the labeling reaction resin column 48, by switching over the three-way valves 52, 47, to dry the labeling reaction resin column 48. Then, the used acetonitrile was discharged into a waste liquid recovery container 54, by switching over the three-way valves 53, 57.

Then, a triflate solution was sucked up from a triflate container 55 by means of the syringe 50, by switching over a three-way valve 56, and then, the thus sucked up triflate solution was passed through the labeling reaction resin column 48, by switching over the three-way valves 56, 52, 47, to perform a labeling reaction of triflate in the labeling reaction resin column 48. Then, a reaction intermediate product containing acetonitrile was sent to the cation-exchange resin column 58, by switching over the three-way valves 53, 57. Then, acetonitrile was evaporated in the cation-exchange resin column 58, and then, the cation-exchange resin column 58 was heated to a temperature of about 130° C. for 10 to 15 minutes to perform a hydrolysis reaction.

After the hydrolysis reaction, germfree water was sucked up from a germfree water container 59 by means of a syringe 60, by switching over a three-way valve 61, and then, the thus sucked up germfree water was sent to the cation-exchange resin column 58, by switching over the three-way valves 61, 57. Then, the reaction product was passed, together with the germfree water, through a refining column 63, by switching over a three-way valve 62, to obtain FDG.

Results of synthesis of FDG according to the FDG synthesizer of the second embodiment of the present invention are shown in Table 3.

TABLE 3

| FDG synthesizer of the prior art | | | FDG synthesizer of the invention | | |
| --- | --- | --- | --- | --- | --- |
| No. | Operation | Time (min:sec) | No. | Operation | Time (min:sec) |
| 1 | Recovery of 0–18 ($^{18}$O) water | 1:38 | 1 | Recovery of 0–18 ($^{18O}$) water | 1:38 |
| 2 | Addition of $K_2CO_3$ | 0:47 | | | |
| 3 | Addition of kryptofix 222 | 0:32 | | | |
| 4 | Evaporation -1 | 3:30 | 2 | Evaporation (Addition of $CH_3CN$) | 3:00 |
| 5 | Addition of acetonitrile | 0:35 | | | |
| 6 | Evaporation -2 | 1:45 | | | |
| 7 | Addition of triflate | 0:56 | | | |
| 8 | Labeling reaction | 5:00 | 3 | Labeling reaction | 1:00 |
| 9 | Addition of water | 0:49 | | | |
| 10 | Collection of SepPak | 1:09 | | | |
| 11 | Addition of water | 0:49 | | | |
| 12 | Washing of SepPak | 1:10 | | | |
| 13 | Extraction of SepPak | 1:22 | | | |
| 14 | Concentration | 2:36 | 4 | Concentration | 2:36 |
| 15 | Addition of hydrochloric acid | 0:35 | | | |
| 16 | Hydrolysis reaction | 10:00 | 5 | Hydrolysis reaction | 10:00 |
| 17 | Elimination of hydrochloric acid | 2:00 | | | |
| 18 | Refining | 1:15 | 6 | Refining | 1:15 |
| | Total time required | 36:28 | | Total time required | 19:29 |

According to the FDG synthesizer of the second embodiment of the present invention, as is clear from Table 3, the FDG synthesizing process can be simplified to about a half that of the prior art, and the total time required for the FDG synthesis is largely reduced. Furthermore, as is clear from Tables 1 and 2, the time required for FDG synthesis in the synthesizer of the second embodiment is shorter by two minutes and 35 seconds than the time required for FDG synthesis in the synthesizer of the first embodiment.

19

EXAMPLE 3

A labeling reaction resin column 48 (refer to FIG. 4) of the third embodiment of the present invention was formed, in the same manner as in the Example 1, by filling a stainless steel cylinder having an inside diameter of 2 mm and a length of 5 cm with a slurry-like mixture which was prepared by mixing 100 to 200 mesh resin powder with a mixed solvent of ethanol and water. A cation-exchange resin column 58' (refer to FIG. 4) of the third embodiment of the present invention was formed, by filling a stainless steel cylinder having an inside diameter of 12 mm and a length of 4 cm with a cation-exchange resin adjusted to an H$^+$ type. A heating means (not shown) for adjusting the temperature in the cation-exchange resin column 58' and a flow rate control means (not shown) for controlling the flow rate of a reaction intermediate product containing an organic solvent passing through the column 58' were provided in the column 58'.

As shown in FIG. 4, a target water, i.e., an irradiated O-18($^{18}$O) water containing an [$^{18}$F] fluoride ion, was sent from a target box 44 to a target water container 45. Then, the target water was sucked up from the target water container 45 by means of a syringe 46, by switching over a three-way valve 47, and then, the thus sucked up target water was sent to the labeling reaction resin column 48 heated to a temperature within a range of from 80 to 100° C. by switching over the three-way valves 47, 52. The [$^{18}$F] fluoride ion was trapped into the resin in the labeling reaction resin column 48, and at the same time, the O-18($^{18}$O) water was separated. Then, the separated O-18($^{18}$O) water was sent to an O-18 ($^{18}$O) water recovery container 49, by switching over a three-way valve 53. Then, acetonitrile was sucked up from an acetonitrile container 51 by means of a syringe 50, by switching over the three-way valves 52, 56, and then, the thus sucked up acetonitrile was passed through the labeling reaction resin column 48, by switching over the three-way valves 52, 47, to dry the labeling reaction resin column 48. Then, the used acetonitrile was discharged into a waste liquid recovery container 54, by switching over the three-way valves 53, 57.

Then, a triflate solution was sucked up from a triflate container 55 by means of the syringe 50, by switching over the three-way valve 56, and then, the thus sucked up triflate solution was passed through the labeling reaction resin column 48, by switching over the three-way valves 56, 52, 47, to perform a labeling reaction of triflate in the labeling reaction resin column 48. Then, a reaction intermediate product containing acetonitrile was sent to the cation-exchange resin column 58', by switching over the three-way valves 53, 57. Then, by operating the flow rate control means (not shown) and the heating means (not shown) described above, the flow rate of the reaction intermediate product containing acetonitrile in the column 58' was adjusted to 0.7 cc/minute, and the temperature in the column 58' was adjusted to about 120° C. As a result, the amount of evaporation per unit time of acetonitrile passing through the column 58' was increased larger than the flow rate per unit time of acetonitrile flowing anew into the column 58'. Therefore, acetonitrile was substantially completely evaporation-eliminated in the cation-exchange resin column 58', and at the same time, the reaction intermediate product could be effectively trapped in the column 58'. Then, the cation-exchange resin column 58' was heated to a temperature of about 130° C. for 10 to 15 minutes to perform a hydrolysis reaction.

After the hydrolysis reaction, germfree water was sucked up from a germfree water container 59 by means of a syringe 60, by switching over a three-way valve 61, and then, the thus sucked up germfree water was sent to the cation-exchange resin column 58', by switching over the three-way valves 61, 57. Then, the reaction product was passed, together with the germfree water, through a refining column 63, by switching over a three-way valve 62, to obtain FDG.

Results of synthesis FDG according to the FDG synthesizer of the third embodiment of the present invention were the same as the results of synthesis in the Example 2 shown in Table 3.

According to the FDG synthesizer of the third embodiment of the present invention, as is clear from Table 3, the FDG synthesizing process can be simplified to about a half that of the prior art, and the total time required for the FDG synthesis is largely reduced, as in the Example 2.

EXAMPLE 4

A cartridge-type labeling reaction resin column 67 (refer to FIG. 5) of the fourth embodiment of the present invention was formed, by filling a stainless steel cylinder having an inside diameter of 2 mm and a length of 5 cm with a slurry-like mixture which was prepared by mixing a 100 to 200 mesh resin powder with a mixed solvent of ethanol and water. A cartridge-type cation-exchange resin column 80 (refer to FIG. 5) of the fourth embodiment of the present invention was formed, by filling a stainless steel cylinder having an inside diameter of 12 mm and a length of 4 cm with a cation-exchange resin adjusted to an H$^+$ type.

As shown in FIG. 5, a target water, i.e., an irradiated O-18($^{18}$O) water containing an [$^{18}$F] fluoride ion was sent from a target box (not shown) to a target water container 64. Then, the target water was sucked up from the target water container 64 by means of a syringe 65, by operating pinch valves P1, P2, and then, the thus sucked up target water was sent to the labeling reaction resin column 67 heated to a temperature within a range of from 80 to 100° C. by operating the pinch valves P1, P2, P6. The [$^{18}$F] fluoride ion was trapped into the resin in the labeling reaction resin column 67, and at the same time, the O-18($^{18}$O) water was separated. Then, the separated O-18($^{18}$O) water was sent to an O-18($^{18}$O) water recovery container (not shown) connected to a connector 68, by operating pinch valves P3, P7, P10. Then, acetonitrile was sucked up from a acetonitrile container 70 by means of a syringe 69, by operating the pinch valves P6, P8, P5, P4, P9, and then, the thus sucked up acetonitrile was passed through the labeling reaction resin column 67, by operating pinch valves P5, P6, P2, to wash the interior of the labeling reaction resin column 67. Then, a helium gas was passed through the labeling reaction resin column 67, by operating pinch valves P8, P6, P2, to sufficiently dry the column 67. On the other hand, the used acetonitrile was discharged into a waste liquid recovery container (not shown) connected to a connector 75, by operating the pinch valves P3, P7, P10, P11.

Then, a triflate solution was sucked up from a triflate container 77 by means of the syringe 69, by operating pinch valves P4, P9, and then, the thus sucked up triflate solution was passed through the labeling reaction resin column 67, by operating the pinch valves P4, P9, P8, P2, to perform a labeling reaction of triflate in the labeling reaction resin column 67. Then, a reaction intermediate product containing acetonitrile was sent to the cation-exchange resin column 80, by operating the pinch valves P3, P7, P10, P11, P13. At this point, the reaction intermediate product containing acetonitrile had a flow rate of 0.7 cc/minute in the column 80, and the temperature in the column 80 was 120° C. Then, a helium gas was passed through the cation-exchange column 80, by operating the pinch valves P10, P11, P13, to evaporation-eliminate acetonitrile remaining in the column 80, and the reaction intermediate product was trapped in the column 80. Then, the cation-exchange resin column 80 was heated to a temperature of about 130° C. for 10 to 15 minutes to perform a hydrolysis reaction. At this point, the pinch valves P7, P10, P11 had been switched over toward the waste liquid recovery container 75.

After the completion of the hydrolysis reaction, germfree water was sucked up from a germfree water container 83 by means of a syringe 84, by operating pinch valves P14, P15, and then, the thus sucked up germfree water was sent to the cation-exchange resin column 80, by operating the pinch valves P15, P14, P13, P11, P10. Then, the reaction product was passed, together with the germfree water, through a refining column 88, by operating pinch valves P12, P16, to obtain FDG.

Results of FDG synthesis according to the FDG synthesizer of the fourth embodiment of the present invention were the same as the results of synthesis in the Example 2 shown in Table 3.

According to the FDG synthesizer of the fourth embodiment of the present invention, as is clear from Table 3, the FDG synthesizing process can be simplified to about a half that of the prior art and the total time required for the FDG synthesis can largely be reduced, as in the Example 2.

EXAMPLE 5

A cartridge-type labeling reaction resin column 67 (refer to FIG. 6) of the fifth embodiment of the present invention was formed, in the same manner as in the Example 4, by filling a stainless steel cylinder having an inside diameter of 2 mm and a length of 5 cm with a slurry-like mixture which was prepared by mixing a 100 to 200 mesh resin powder with a mixed solvent of ethanol and water. A cartridge-type cation-exchange resin column 80 (refer to FIG. 6) of the fifth embodiment of the present invention was formed, in the same manner as in the Example 4, by filling a stainless steel cylinder having an inside diameter of 12 mm and a length of 4 cm with a cation-exchange resin adjusted to an $H^+$ type.

As shown in FIG. 6, a target water, i.e., an irradiated O-18($^{18}$O) water containing an fluoride ion was sent from a target box (not shown) to a target water container 64. Then, the target water was sucked up from the target water container 64 by means of a syringe 65, by switching over a three-way valve 66, and then, the thus sucked up target water was sent to the labeling reaction resin column 67 heated to a temperature within a range of from 80 to 100° C. by switching over the three-way valves 66, 72. The [$^{18}$F] fluoride ion was trapped into the resin in the labeling reaction resin column 67, and at the same time, the O-18 ($^{18}$O) water was separated. Then, the separated O-18($^{18}$O) water was sent to an O-18($^{18}$O) water recovery container (not shown) connected to a connector 68, by switching over a three-way valve 74. Then, acetonitrile was sucked up from a acetonitrile container 70 by means of a syringe 69, by switching over the three-way valves 71, 76, and then, the thus sucked up acetonitrile was passed through the labeling reaction resin column 67, by switching over the three-way valves 71, 73, 72, to wash the interior of the labeling reaction resin column 67. Then, helium gas was passed through the labeling reaction resin column 67, by switching over the three-way valves 72, 73, to sufficiently dry the column 67. On the other hand, the used acetonitrile was discharged into a waste liquid recovery container (not shown) connected to a connector 75, by switching over the three-way valves 74, 78.

Then, a triflate solution was sucked up from a triflate container 77 by means of the syringe 69, by switching over a three-way valve 76, and then, the thus sucked up triflate solution was passed through the labeling reaction resin column 67, by switching over the three-way valves 76, 71, 73, 72, to perform a labeling reaction of triflate in the labeling reaction resin column 67. Then, a reaction intermediate product containing acetonitrile was sent to the cation-exchange resin column 80, by switching over the three-way valves 74, 78, 79. At this point, the reaction intermediate product containing acetonitrile had a flow rate of 0.7 cc/minute in the column 80, and the temperature in the column 80 was 120° C. Then, helium gas was passed through the cation-exchange resin column 80, by switching over the three-way valves 79, 81, to evaporation-eliminate acetonitrile remaining in the column 80, and the reaction intermediate product was trapped in the column 80. Then, the cation-exchange resin column 80 was heated to a temperature of about 130° C. for 10 to 15 minutes to perform a hydrolysis reaction.

After the completion of the hydrolysis reaction, germfree water was sucked up from a germfree water container 83 by means of a syringe 84, by switching over a three-way valve 85, and then, the thus sucked up germfree water was sent to the cation-exchange resin column 80, by switching over the three-way valves 85, 81, 79. Then, the reaction product was passed, together with the germfree water, through a refining column 88, by switching over a three-way valve 82, to obtain FDG.

Results of FDG synthesis according to the FDG synthesizer of the fifth embodiment of the present invention were the same as the results of synthesis in the Example 2 shown in Table 3.

According to the FDG synthesizer of the fifth embodiment of the present invention, as is clear from Table 3, the FDG synthesizing process can be simplified to about a half that of the prior art, and the total time required for the FDG synthesis can largely be reduced as in the Example 2.

According to the FDG synthesizer of the present invention, as described above in detail, there is provided an FDG synthesizer, in which a synthesis process of FDG is simplified, with an improved yield of a synthesis product, and the time of synthesis is largely reduced, thus providing many industrially useful effects.

What is claimed is:

1. An FDG synthesizer, which comprises:

a labeling reaction resin column in which (i) target water containing fluoride ion and (ii) a triflate solution are passed through said labeling reaction resin column, said labeling reaction resin column comprising a column filled with a polymer-supporter phase-transfer catalyst resin, for trapping the fluoride ion contained in the target water, and wherein a labeling reaction is performed between the thus trapped fluoride ion and the triflate, and a hydrolysis reaction vessel for receiving a reaction intermediate product obtained from the labeling reaction, and wherein a hydrolysis reaction is performed by the addition of a strong acidic aqueous solution or a strong alkaline aqueous solution.

2. The FDG synthesizer as claimed in claim 1, wherein:

said polymer-supported phase-transfer catalyst resin comprises a phosphonium salt fixed to a polystyrene resin.

3. An FDG synthesizer, which comprises:

a labeling reaction resin column in which (i) target water containing fluoride ion and (ii) a triflate solution are passed through said labeling reaction resin column, said labeling reaction resin column comprising a column filed with a polymer-supporter phase-transfer catalyst resin for trapping the fluoride ion contained in the target water, and wherein a labeling reaction is performed between the thus trapped fluoride ion and the triflate, and a cation-exchange resin column for receiving a reaction intermediate product obtained from the labeling reaction, and wherein a hydrolysis reaction is performed by bringing the reaction intermediate product into contact with a cation-exchange resin adjusted to an $H^+$ cation-exchange resin in the cation-exchange resin column.

4. The FDG synthesizer as claimed in claim 3, wherein:

the cation-exchange resin column has a heating means and a flow rate control means for controlling the flow of said reaction intermediate product which contains an organic solvent, and in said cation-exchange resin column, said reaction intermediate product containing said organic solvent obtained from said labeling reaction is heated, to evaporation-eliminate said organic solvent by the heating means in the cation-exchange resin column, and at the same time, said reaction intermediate product after the elimination of said organic solvent is brought into contact with the cation-exchange resin adjusted to an $H^+$ cation-exchange resin in the cation-exchange resin column to perform said hydrolysis reaction.

5. The FDG synthesizer as claimed in claim 4, wherein the heating means for the cation-exchange resin column heats the cation-exchange resin column from 90 to 150° C., and wherein the flow rate control means controls the flow of the reaction intermediate product from 0.5 to 1.5 cc/minute.

6. An FDG synthesizer, which comprises:

(a) a cartridge labeling reaction resin column, (b) a cartridge cation-exchange resin column, and (c) a disposable cartridge base into which passageways and switchover valves for communicating said labeling reaction resin column with said cation-exchange resin column, are incorporated; in said cartridge labeling reaction resin column (i) target water containing fluoride ion and (ii) a triflate solution are passed through, said cartridge labeling reaction resin column comprising a disposable column filled with a polymer-supported phase-transfer catalyst resin, said cartridge labeling reaction resin column being one-touch-releasably attachable to said disposable cartridge base, for trapping the fluoride ions contained in the target water, and wherein a labeling reaction between the thus trapped fluoride ion and the triflate take place; and said cartridge cation-exchange resin column comprising a disposable column filled with a cation-exchange resin adjusted to an $H^+$ cation-exchange resin, said cartridge cation-exchange resin column being one-tough-releasably attachable to said disposable cartridge base, and wherein a reaction intermediate product obtained from said labeling reaction is brought into contact with said cation-exchange resin adjusted to said $H^+$ cation-exchange resin in said cation-exchange resin column to perform a hydrolysis reaction.

7. The FDG synthesizer as claimed in claim 6, wherein: each of said switchover valves includes a three-way cock therein.

8. The FDG synthesizer as claimed in claim 6, wherein the synthesizer body comprises a means for driving the switchover valves and a means for heating the cartridge labeling reaction resin column and the cartridge cation-exchange resin column.

9. The FDG synthesizer as claimed in claim 6, wherein the passageways comprise a teflon tube.

10. The FDG synthesizer as claimed in claim 6, wherein the passageways comprise a polypropylene tube.

* * * * *